US008667293B2

(12) United States Patent
Birtwhistle et al.

(10) Patent No.: US 8,667,293 B2
(45) Date of Patent: Mar. 4, 2014

(54) CRYPTOGRAPHIC DATA DISTRIBUTION AND REVOCATION FOR HANDHELD MEDICAL DEVICES

(75) Inventors: Daniel Birtwhistle, Fishers, IN (US);
James Tenbarge, Fishers, IN (US);
Ulrich Porsch, Weinheim (DE);
Kai-Oliver Schwenker, Hassloch (DE);
Eric Rachner, Seattle, WA (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 179 days.

(21) Appl. No.: 13/207,934

(22) Filed: Aug. 11, 2011

(65) Prior Publication Data

US 2013/0042117 A1     Feb. 14, 2013

(51) Int. Cl.
*G06F 21/00*     (2013.01)

(52) U.S. Cl.
USPC ............... 713/182; 705/1.1; 705/2; 705/3; 705/14.27; 705/74; 235/375; 235/377; 235/382; 607/30; 607/59; 607/60

(58) Field of Classification Search
USPC ........... 713/182; 705/1.1, 14.27, 74, 2–3; 235/375, 377, 382; 607/30, 59, 60
See application file for complete search history.

(56) References Cited

U.S. PATENT DOCUMENTS

| | | | |
|---|---|---|---|
| 7,167,755 B2 | 1/2007 | Seeberger et al. | |
| 7,200,578 B2 * | 4/2007 | Paltenghe et al. | 705/74 |
| 7,761,167 B2 * | 7/2010 | Bennett et al. | 607/60 |
| 8,095,692 B2 | 1/2012 | Mehta et al. | |
| 8,265,957 B2 * | 9/2012 | Craine | 705/3 |
| 2004/0003266 A1 | 1/2004 | Moshir et al. | |
| 2005/0120106 A1 | 6/2005 | Albertao | |

FOREIGN PATENT DOCUMENTS

EP     1684172     7/2006

OTHER PUBLICATIONS

Internet X.509 Public Key Infrastructure Certificate and Certificate Revocation List Profile; May 1, 2008, XP015057243, ISSN: 0000-0003.

* cited by examiner

*Primary Examiner* — Thanhnga B Truong
(74) *Attorney, Agent, or Firm* — Harness, Dickey

(57) ABSTRACT

A method includes: receiving a revocation list from a remote data server at a configuration device. The revocation list includes N cryptographic certificates associated with N computer software entities, respectively, that are not to be executed by any of a group of medical devices including a handheld medical device. N is an integer greater than or equal to zero The method further includes receiving data from the handheld medical device at the configuration device. The data includes a cryptographic certificate that is associated with a given computer software entity that is presently installed in memory of the handheld medical device for execution by the handheld medical device. The method further includes comparing the cryptographic certificate with the revocation list; and selectively executing a protective function by the configuration device when the cryptographic certificate is the same as one of the N cryptographic certificates of the revocation list.

20 Claims, 7 Drawing Sheets

CRYPTOGRAPHIC DATA DISTRIBUTION AND REVOCATION FOR HANDHELD MEDICAL DEVICES

FIELD

The present disclosure relates to handheld medical devices and more particularly to data distribution and revocation systems and methods for handheld medical devices.

BACKGROUND

Diabetes mellitus, often referred to as diabetes, is a chronic condition in which a person has elevated blood glucose levels that result from defects in the body's ability to produce and/or use insulin. There are three main types of diabetes. Type 1 diabetes usually strikes children and young adults, and can be autoimmune, genetic, and/or environmental. Type 2 diabetes accounts for 90-95% of diabetes cases and is linked to obesity and physical inactivity. Gestational diabetes is a form of glucose intolerance diagnosed during pregnancy and usually resolves spontaneously after delivery.

In 2009, according to the World Health Organization, at least 220 million people worldwide suffer from diabetes. In 2005, an estimated 1.1 million people died from diabetes. The incidence of diabetes is increasing rapidly, and it is estimated that between 2005 and 2030, the number of deaths from diabetes will double. In the United States, nearly 24 million Americans have diabetes with an estimated 25 percent of seniors age 60 and older being affected. The Centers for Disease Control and Prevention forecast that 1 in 3 Americans born after 2000 will develop diabetes during their lifetime. The National Diabetes Information Clearinghouse estimates that diabetes costs $132 billion in the United States alone every year. Without treatment, diabetes can lead to severe complications such as heart disease, stroke, blindness, kidney failure, amputations, and death related to pneumonia and flu.

Management of diabetes is complex because the level of blood glucose entering the bloodstream is dynamic. Variation of insulin in the bloodstream that controls the transport of glucose out of the bloodstream also complicates diabetes management. Blood glucose levels are sensitive to diet and exercise, but also can be affected by sleep, stress, smoking, travel, illness, menses, and other psychological and lifestyle factors that are unique to each patient. The dynamic nature of blood glucose and insulin, and all other factors affecting blood glucose, often require a person with diabetes to forecast blood glucose levels. Administration of insulin and/or oral medications can be regulated and timed to maintain blood glucose levels within an appropriate range at all times.

Management of diabetes is often highly intrusive because of the need to consistently obtain reliable diagnostic information, follow prescribed therapy, and manage lifestyle on a daily basis. Diagnostic information, such blood glucose level, can be obtained from a capillary blood sample with a lancing device and a test strip. The blood glucose level is measured via the test strip using a handheld blood glucose meter. Interstitial glucose levels can be obtained from a continuous glucose sensor worn on the body.

A therapy regimen for a patient can be established based on one or more of the patient's blood glucose levels. The therapy regimen can include administration of insulin and/or oral medication. Insulin can be administered with a syringe, an insulin pen, an ambulatory infusion pump, or a combination of two or more of the above. With insulin therapy, determining the amount of insulin to inject at a given time can require forecasting meal amount and composition (e.g., of fat, carbohydrates, and proteins, and amounts of each). Determining the amount of insulin to inject at a given time can also require consideration of the effects of exercise and physiologic state. The patient's management of lifestyle factors such as body weight, diet, and exercise can significantly influence the type and effectiveness of therapy.

Management of diabetes involves large amounts of diagnostic data and prescriptive data that are acquired from medical devices, personal health care devices, patient recorded information, health care professional tests results, prescribed medications and recorded information. Medical devices including self-monitoring bG meters, continuous glucose monitors, insulin infusion pumps, diabetes analysis software, and diabetes device configuration software each of which generates or manages or both large amounts of diagnostic and prescriptive data. Personal health care devices can include weights, scales, blood pressure cuffs, pedometers, other activity monitors, and other suitable devices. Patient recorded data can include information relating to meals, exercise, and lifestyle. Health care professional biomarker data can include HbA1C, cholesterol, triglycerides, fasting glucose, and glucose tolerance. Health care professional recorded information can include therapy and other patient-specific information.

Over time, a handheld medical device may become outdated. One or more updates to software executed by a handheld medical device may be desirable under some circumstances. Thus, there is a need for a system that provides the ability to update handheld medical devices. Additionally, there is a need for a system that provides the ability to update handheld medical devices securely.

The background description provided herein is for the purpose of generally presenting the context of the disclosure. Work of the presently named inventors, to the extent it is described in this background section, as well as aspects of the description that cannot otherwise qualify as prior art at the time of filing, are neither expressly nor impliedly admitted as prior art against the present disclosure.

SUMMARY

In a feature, a method of protecting a handheld medical device from executing a computer software entity installed in memory of the handheld medical device for execution by the handheld medical device is provided. The method includes: receiving a revocation list from a remote data server at a configuration device. The revocation list includes N cryptographic certificates associated with N computer software entities, respectively, that are not to be executed by any of a group of medical devices including a handheld medical device. N is an integer greater than or equal to zero The method further includes receiving data from the handheld medical device at the configuration device. The data includes a cryptographic certificate that is associated with a given computer software entity that is presently installed in memory of the handheld medical device for execution by the handheld medical device. The method further includes comparing the cryptographic certificate with the revocation list; and selectively executing a protective function by the configuration device when the cryptographic certificate is the same as one of the N cryptographic certificates of the revocation list.

In another feature, a method of regulating updatability of data stored in memory of a handheld medical device is provided. The method includes: receiving a revocation list from a first remote data server at a configuration device. The revocation list includes N cryptographic certificates associated with N handheld medical devices, respectively, that are to be denied access to data accessible via a second remote data server. N is an integer greater than or equal to zero. The method further includes receiving data from a handheld medical device at the configuration device. The data includes a cryptographic certificate that is associated with the handheld medical device. The method further includes comparing the cryptographic certificate with the revocation list; and selectively updating the handheld medical device with data from the second remote data server after a determination that the cryptographic certificate is not the same as any of the N cryptographic certificates of the revocation list.

Further areas of applicability of the present disclosure will become apparent from the detailed description provided hereinafter. It should be understood that the detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein.

DETAILED DESCRIPTION

Figure 1:
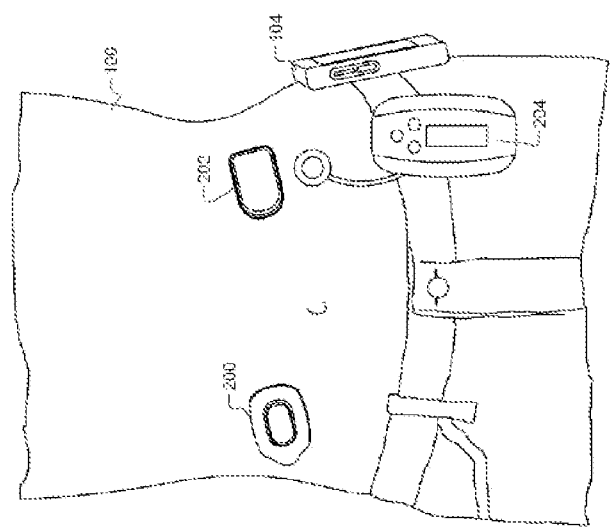
FIG. 1 shows a patient and a health care professional along with various devices that can be used to help the patient monitor and control health.

The following description is merely illustrative in nature and is in no way intended to limit the disclosure, its application, or uses. For purposes of clarity, the same reference numbers will be used in the drawings to identify similar elements. As used herein, the phrase at least one of A, B, and C should be construed to mean a logical (A or B or C), using a non-exclusive logical or. It should be understood that steps within a method can be executed in different order without altering the principles of the present disclosure.

Referring now to FIG. 1, a patient 100 with diabetes and a health care professional 102 are shown in a clinical environment. The patient 100 with diabetes can be diagnosed with a metabolic syndrome, pre-diabetes, type 1 diabetes, type 2 diabetes, gestational diabetes, etc. Healthcare providers for diabetes are diverse and include nurses, nurse practitioners, physicians, endocrinologists, and others and are collectively referred to as health care professionals.

During a health care consultation, the patient 100 typically shares with the health care professional 102 a variety of data including blood glucose (bG) measurements, continuous glucose monitor data, amounts and type of insulin administered, amounts of food and beverages consumed, exercise schedules, health status, and other lifestyle information. The health care professional 102 can obtain additional data for the patient 100, such as measurements of HbA1C, cholesterol levels, plasma glucose, triglycerides, blood pressure, and weight. The data can be recorded manually or electronically on a handheld diabetes management device 104 (e.g., a handheld bG monitor device), a diabetes analysis software executed on a personal computer (PC) 106, and/or a web-based diabetes analysis site. The health care professional 102 can analyze the patient data manually or electronically using the diabetes analysis software and/or the web-based diabetes analysis site. After analyzing the data and reviewing how efficacious previously prescribed therapy is and how well the patient 100 followed the previously prescribed therapy, the health care professional 102 can decide whether to modify a therapy prescribed for the patient 100.

Figure 2:
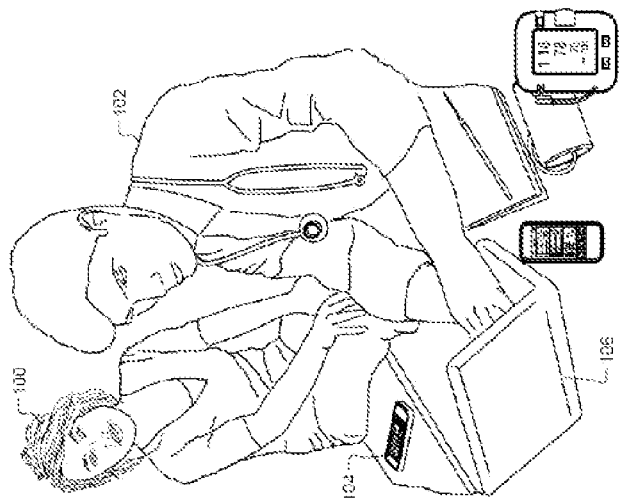
FIG. 2 shows a patient with a continuous glucose monitor (CGM), an ambulatory durable insulin infusion pump, an ambulatory non-durable insulin infusion pump, and a blood glucose (bG) management device.

Referring now to FIG. 2, the patient 100 can use a continuous glucose monitor (CGM) 200, an ambulatory durable insulin infusion pump 204 or an ambulatory non-durable insulin infusion pump 202 (collectively insulin pump 204), and the diabetes management device 104. The CGM 200 can use a subcutaneous sensor to sense and monitor the amount of glucose (e.g., glucose concentration) of the patient 100. The CGM 200 communicates glucose measurements to the diabetes management device 104.

The diabetes management device 104 performs various tasks including measuring and recording bG measurements, determining an amount of insulin to be administered to the patient 100 via the insulin pump 204, receiving user input via a user interface, archiving data, performing structured bG tests, etc. The diabetes management device 104 can transmit instructions to the insulin pump 204, and the insulin pump 204 selectively delivers insulin to the patient 100. Insulin can be delivered in the form of a meal bolus dose, a correction bolus dose, a basal dose, etc.

Figure 3:
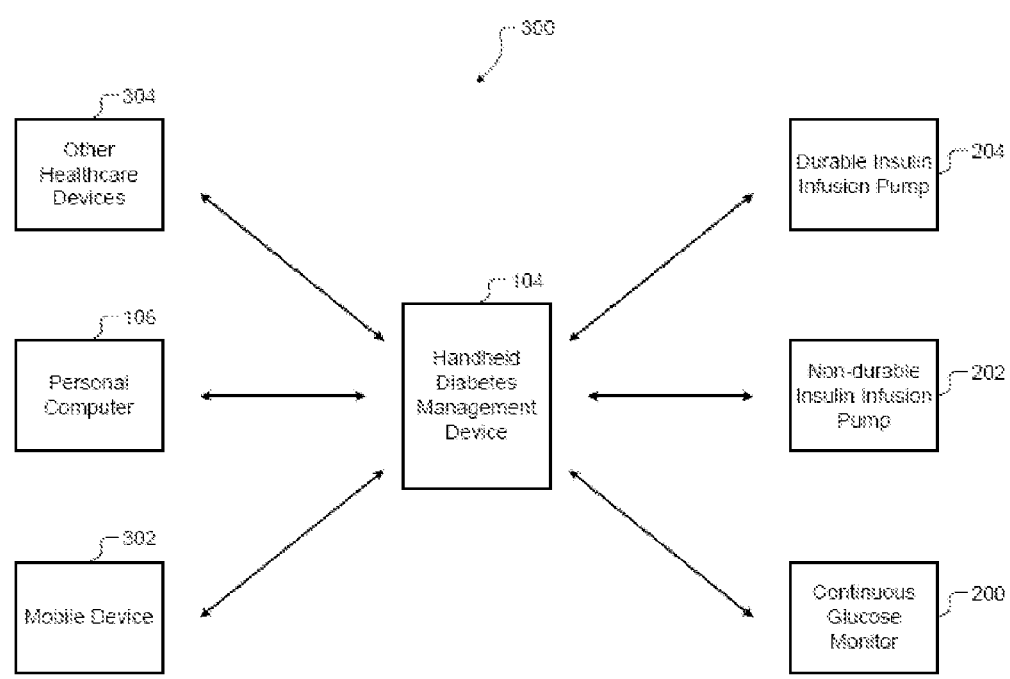
FIG. 3 shows a diabetes care system of systems that can be used to manage diabetes.

Referring now to FIG. 3, a diabetes management system 300 is shown which can be used by the patient 100 and/or the health care professional 102. The system 300 can include one or more of the following devices: the diabetes management device 104, the CGM 200, the insulin pump 204, a mobile device 302, the diabetes management software executed on the computer 106, and one or more other health care devices 304. The diabetes management device 104 can be configured as a system "hub" and communicate with one or more of the other devices of the system 300. The insulin pump 204, the mobile device 302, or another suitable device can alternatively serve as the system hub. Communication between various devices in the system 300 can be performed using wireless interfaces (e.g., Bluetooth) and/or wired interfaces (e.g., USB). Communication protocols used by these devices can include protocols compliant with the IEEE 11073 standard as extended using guidelines provided by Continua Health Alliance Design Guidelines. Further, health care records systems such as Microsoft HealthVault™ and Google Health™ can be used by the patient 100 and the health care professional 102 to exchange information.

The diabetes management software running on the computer 106 can include an analyzer-configurator that stores configuration information for devices of the system 300. For example only, the configurator has a database to store configuration information for the diabetes management device 104 and the other devices. A patient can interface the configurator through standard web based or computer graphical user interfaces (GUIs). The configurator selectively transmits patient-approved configurations to the devices of the system 300. The analyzer selectively retrieves data from the devices of the system 300, stores the data in a database, selectively analyzes the data, and outputs analysis results through standard web based or computer GUIs.

Figure 4:
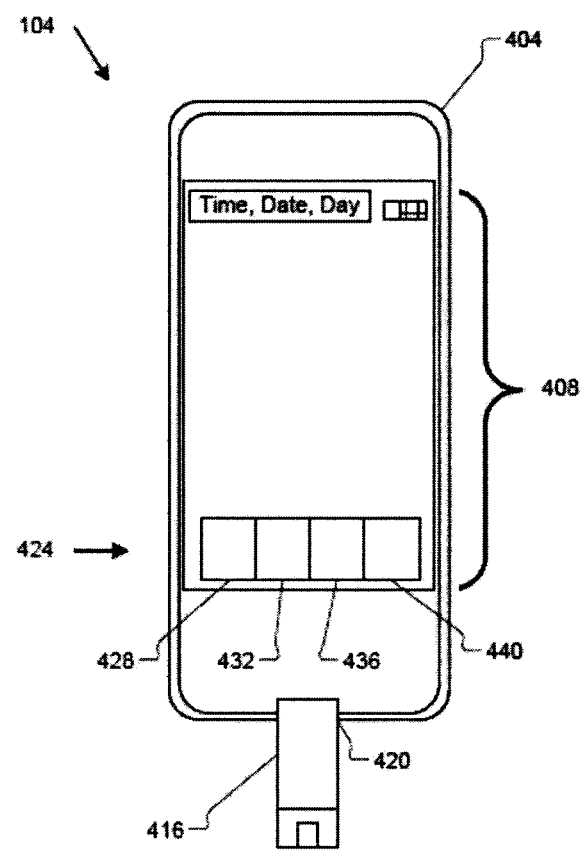
FIG. 4 is a high level diagram of an example implementation of a handheld diabetes management device.

Referring now to FIG. 4, a high level illustration of an example embodiment of the diabetes management device 104 is presented. The diabetes management device 104 includes, among other things, a housing 404, user unit control switches (not specifically numbered), a touchscreen display 408, and a bG test strip port 420. The user unit control switches, for example, can include ON/OFF switches, volume switches, alarm switches for bG testing and/or insulin administration, and/or one or more other switches or other types of control devices that a patient can use to control functions/operations of the diabetes management device 104.

A bG test strip 416 can be inserted into the bG test strip port 420. The bG test strip 416 can be inserted into the bG test strip port 420 by a patient, from a test strip drum (not shown) located within the housing 404, or in another suitable manner. The bG test strip 416 is shown already inserted into the bG test strip port 420 in the example of FIG. 4 and not yet inserted into the bG test strip port 420 in the example of FIG. 5.

User selectable options 424 can be displayed on a portion of the display 408. The selectable options 424 can include a menu option 428, a bolus insulin option 432, a carbohydrate option 436, and an event option 440. One or more other user selectable options can additionally or alternatively be available. The patient can access a device menu for the diabetes management device 104 by selecting the menu option 428. The patient can input various insulin (and/or other medication) information (e.g., amount, insulin type, etc.) by selecting the bolus insulin option 432. The patient can input various carbohydrate intake information (e.g., amount) by selecting the carbohydrate option 436. The patient can also input other food intake information (e.g., protein content, fat content, etc.) by selecting the carbohydrate option 436. The patient can input various event related information (e.g., meals, exercise, periods of stress, etc.) that can affect the patient's bG measurements by selecting the event option 440.

Although the display 408 is described herein as a touchscreen display, the diabetes management device 104 can include another suitable form of display (e.g., LED, etc.). If a touchscreen display is not used, the user control switches can include specific buttons or controls by which the patient is able to select various options and input markers needed to operate the diabetes management device 104.

The above description is a broad description of the diabetes management device 104. In practice, the diabetes management device 104 can include additional controls, input ports, output ports, etc., as can be desired to further enhance its utility or its use with other components and devices (e.g., computers, infusion pumps, cellular phones, etc.). The description of the diabetes management device 104 should not be taken as limiting as to the construction of the diabetes management device 104 or as to the features and capabilities of the diabetes management device 104.

As used herein, the term "module" can refer to, be part of, or include an Application Specific Integrated Circuit (ASIC); an electronic circuit; a combinational logic circuit; a field programmable gate array (FPGA); a processor (shared, dedicated, or group) that executes code; other suitable components that provide the described functionality; or a combination of some or all of the above, such as in a system-on-chip. The term "module" can include memory (shared, dedicated, or group) that stores code executed by the processor.

The term "code," as used above, can include software, firmware, and/or microcode, and can refer to programs, routines, functions, classes, and/or objects. The term "shared," as used above, means that some or all code from multiple modules can be executed using a single (shared) processor. In addition, some or all code from multiple modules can be stored by a single (shared) memory. The term "group," as used above, means that some or all code from a single module can be executed using a group of processors. In addition, some or all code from a single module can be stored using a group of memories.

The apparatuses and methods described herein can be implemented by one or more computer programs executed by one or more processors. The computer programs include processor-executable instructions that are stored on a non-transitory, tangible, computer readable medium. The computer programs can also include stored data. Examples of the non-transitory, tangible, computer readable medium include, but are not limited to, nonvolatile memory, magnetic storage, and optical storage.

Figure 5:
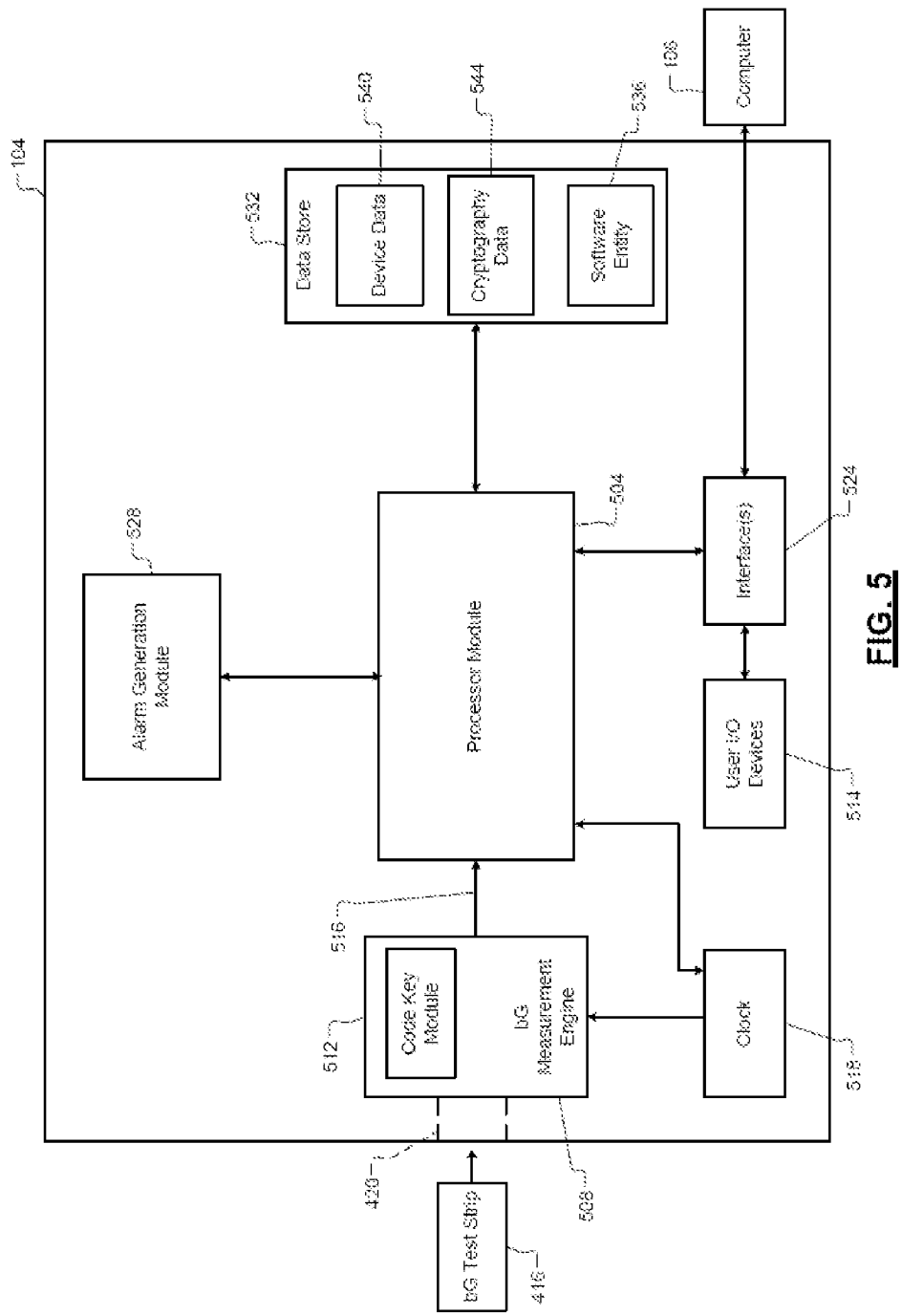
FIG. 5 includes a functional block diagram of an example implementation of a handheld diabetes management device.

Referring now to FIG. 5, a functional block diagram of the diabetes management device 104 is presented. While the present disclosure will be discussed in conjunction with the diabetes management device 104, the present disclosure is also applicable to other handheld medical devices, including insulin pumps, CGMs, and other types of handheld medical devices.

The diabetes management device 104 can include a processor module (e.g., a microprocessor based subsystem) 504 that can receive information from a bG measurement engine 508. The bG measurement engine 508 can be located adjacent the bG test strip port 420. The bG measurement engine 508 reads (measures) a bG level of the bG test strip 416 inserted into the bG test strip port 420. The bG measurement engine 508 can include a code key module 512 that includes pre-calibrated data for determining a bG level from the bG test strip 416. The bG test strip 416 may be provided from the test strip drum housing unused bG test strips within the diabetes management device 104.

The bG measurement engine 508 generates bG sample data 516 based on its reading of the bG test strip 416. Among other things, the bG sample data 516 includes data indicative of the bG level of a blood sample on the bG test strip 416. The processor module 504 can also receive bG sample data from other sources, such as via the CGM 200, the display 408, and/or another suitable source. The processor module 504 can receive user input data via one or more user input/output (I/O) devices 514, such as the display 408, one or more buttons/switches/etc., and/or one or more other user I/O devices.

The bG measurement engine 508 can also generate the bG sample data 516 to indicate the date and time when the bG test strip 416 was read. In other words, the bG measurement engine 508 can include a time stamp with the bG sample data 516. In various implementations, the processor module 504 can selectively time stamp the bG sample data 516 and can time stamp user input data and other data when it is received.

A clock 518 can provide the date and time. The patient can configure the present date and time, and the clock 518 thereafter tracks the present date and time. In various implementations, the present date and time can be acquired from (e.g., synchronized with) the computer 106.

The diabetes management device 104 includes a datastore 532. For example only, the datastore 532 may include memory and/or one or more other suitable tangible, computer readable mediums. Various data may be stored in the datastore 532. For example only, a computer software entity 536 is stored in the datastore 532. The computer software entity 536 may include, for example, firmware, software, variables, etc. The processor module 504 selectively executes portions of the computer software entity 536 to perform the functions of the diabetes management device 104.

The computer software entity 536 may be written to the datastore 532 before the diabetes management device 104 is released to the public. The computer software entity 536 may be updated after the diabetes management device 104 is released. The computer software entity 536 may be updated, for example, via software running on the computer 106 or via a remote data server (see also FIG. 6B).

Device data 540 may also be stored in the datastore 532. The device data 540 may include, for example, product type data, product version data, region data, a software certificate, a unique device identifier, a device/user certificate, and other suitable device specific data. The product type data may indicate, for example, bG management device, insulin pump, CGM, etc. The product version data may indicate, for example, a version (or generation) of the diabetes management device 104, a model name/number, etc. The software certificate may include, for example, a version or identifier of the computer software entity 536 and other suitable data. The software certificate is a cryptographic (digital) certificate. The software certificate may also be referred to as a code certificate. The unique device identifier may include data that is unique to the diabetes management device 104, such as a serial number or another suitable unique identifier. The device/user certificate is a cryptographic (digital) certificate that is unique to the diabetes management device 104.

Cryptographic data 544 may also be stored in the datastore 532. The cryptographic data 544 may be used, for example, in encrypting messages transmitted by the diabetes management device 104 to another device, decrypting messages received by the diabetes management device 104 from another device, authentication, verification, and other cryptographic functions. For example only, the cryptographic data 544 may include one or more keys (e.g., public), one or more encryption algorithms, one or more decryption algorithms, and other suitable cryptographic data.

Figure 6A:
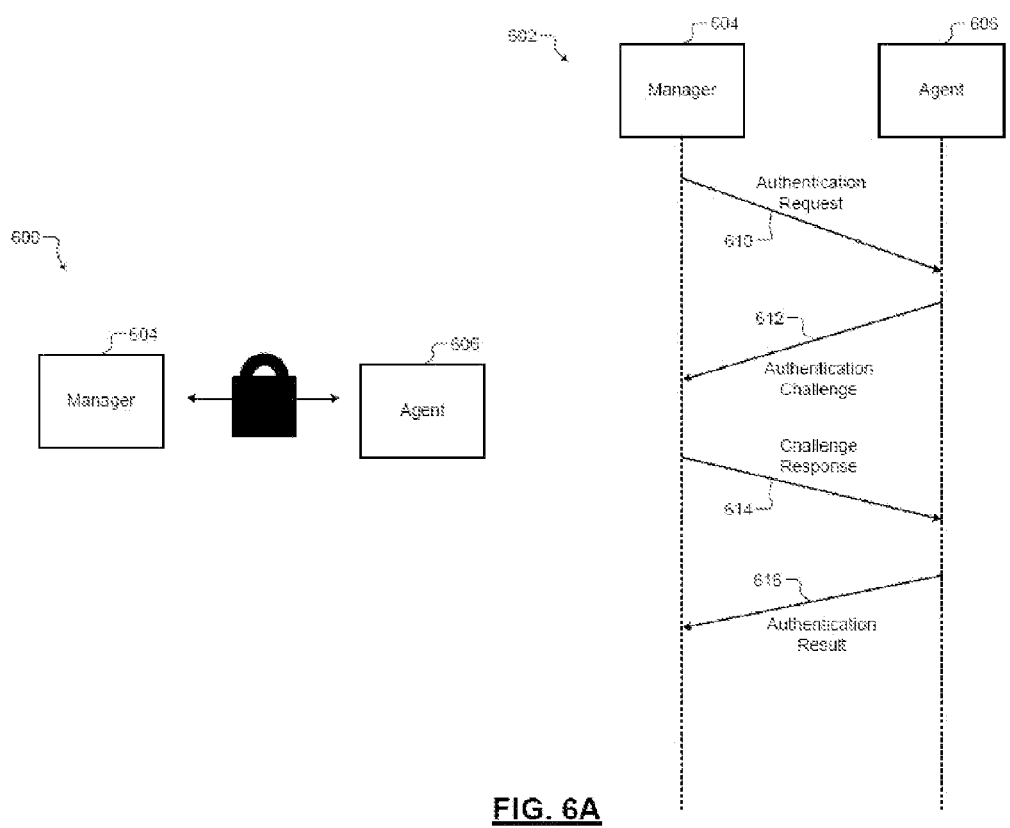
FIG. 6A includes example illustrations of secure communication systems and methods.

Referring now to FIG. 6A, example implementations of a secure communication system 600 and a secure communication method 602 are presented. The secure communication system 600 includes a manager 604 and an agent 606. The manager 604 may communicate with one or more other agents, and the agent 606 may communicate with one or more other managers. Communication between the manager 604 and the agent 606 will be discussed, but the following discussion is applicable to communication between other managers and agents.

The manager 604 and the agent 606 may communicate, for example, in conjunction with the manager 604 updating data stored in memory of the agent 606. However, communication between the manager 604 and the agent 606 is performed according to a protocol to ensure that the communication is secure. The protocol may conform with the RSA Cryptography Standard according to RSA Laboratories Public Key Cryptography Standards (PKCS) volume #1 or another suitable cryptographic protocol. The protocol may involve use of an SHA-2 (e.g., SHA-256) cryptographic hash algorithm, an SHA-3 cryptographic hash algorithm, or another suitable cryptographic hash algorithm.

Managers may each be attributed with one of a plurality of different roles. A manager serving as a role may be able to update predetermined types of data stored in the memory of the agent 606. Each different role may be associated with the ability to update different predetermined types of data. The ability to update different types of data may be based on the principle of least privilege. More specifically, a manager serving under a first role may be able to update a first set of types of data stored in the memory of the agent 606. A manager serving under a second role may be able to update the first set of types of data and, in addition, be able to update a second set of types of data stored in the memory of the agent 606. A manager serving under a third role may be able to update a third set of types of data in addition to the first and second sets of types and so on. Agents may be configured to accept updates only from managers serving under one or more of the plurality of roles.

The manager 604 has a public cryptographic key. The manager 604 also has a private cryptographic key. The private cryptographic key also include data regarding the public cryptographic key. The manager 604 cryptographically signs messages that it transmits to the agent 606 using the private key and an encryption algorithm. The agent 606 uses the public key and a decryption algorithm to verify that the signed message was sent by a trusted source (e.g., the manager 604) and that the signed message not altered before receipt by the agent 606. The process of signing a message and verifying that the signed message was sent by a trusted source may be performed as part of an authentication procedure. The manager 604 and the agent 606 may perform authentication to ensure that communication between the manager 604 and the agent 606 is secure before the manager 604 can update data stored in the memory of the agent 606.

An example of authentication is illustrated by 602. The manager 604 may transmit an authentication request 610 to the agent 606 to initiate the authentication of secure communication between the manager 604 and the agent 606. The authentication request 610 may include, for example, the role of the manager 604, the public key, and/or other suitable data. In various implementations, the authentication request 610 may be in the form of a digital certificate.

The agent 606 may determine whether the agent 606 is configured to accept updates from the role of the manager 604. If not, the agent 606 may transmit a predetermined error code to the manager 604 and terminate the authentication. If so, the agent 606 may generate an authentication challenge 612 and transmit the authentication challenge 612 to the manager 604. The agent 606 generates the authentication challenge 612 randomly. For example only, the agent 606 may generate the authentication challenge 612 randomly using a random number generator, such as a random number generator that complies with NIST Special Publication 800-90, titled Recommendation for Random Number Generation Using Deterministic Random Bit Generators (March 2007).

The manager 604 digitally signs the authentication challenge 612 using the private key and transmits the signed authentication challenge to the agent 606 in the form of a challenge response 614. Based on the public key and the authentication challenge 612, the agent 606 determines whether the challenge response 614 is authentic. In other words, the agent 606 verifies the signature using the public key and the authentication challenge 612. The agent 606 notifies the manager 604 whether the authentication passed or failed via an authentication result 616.

If the authentication passed, the manager 604 may selectively update data stored in the memory of the agent 606. Authentication may also be performed between the manager 604 and a server (e.g., FIG. 6B) to ensure secure communication between the manager 604 and the server. Before the manager 604 creates or modifies a file to be uploaded to the agent 606, the manager 604 signs the file using the private key associated with its role. The manager 604 may sign the file using the private key, RSA, and the SHA-2 algorithm. The result of the signature is a signed hash of the data being signed. The private key associated with one or more of the roles may be ineligible for using to sign a file.

When the agent 606 receives a file from the manager 604, the agent 606 verifies the digital signature provided with the file. The manager 604 may notify the agent 606 which public key to use to verify the signature. The agent 606 may verify the file (or other incoming signed data, such as the challenge response 614) by calling an application programming interface (API) used for verification. The agent 606 may provide the public key, the signed file, and the original data for the API. The algorithms to be used by the API may also be specified, and the algorithms may be, for example, RSA and the SHA-2 algorithm. The agent 606 may avoid using the transmitted data if the verification fails.

Figure 6B:
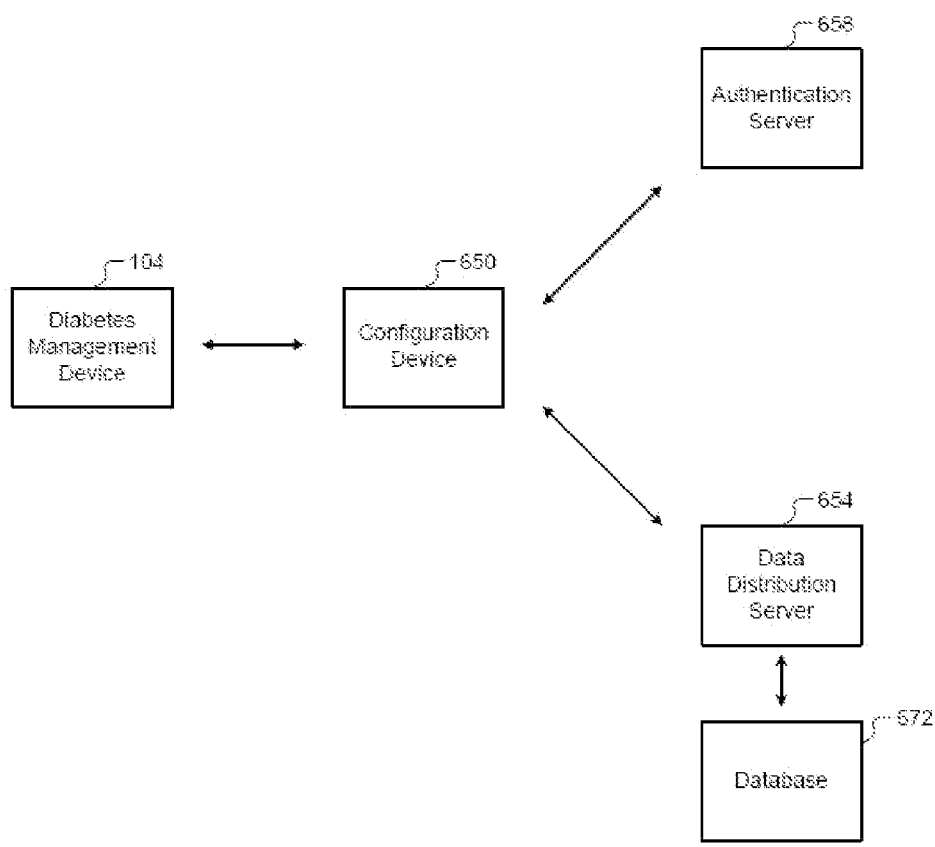
FIG. 6B includes a functional block diagram of an example data distribution system.

Referring now to FIG. 6B, a functional block diagram of an example data distribution system is presented. Examples of the agent 606 may be the diabetes management device 104, the insulin pump 204, the CGM 200, the mobile device 304, and other handheld medical devices. An examples of the manager 604 may be a configuration device 650. For example only, the configuration device 650 may include an application (e.g., software) executed on a computer, such as the computer 106. The computer software entity 536 stored in the datastore 532 of the diabetes management device 104 may be updated. The computer software entity 536 may be updated in response to a user input request to update the computer software entity 536 when the diabetes management device 104 is connected to the configuration device 650. A user can input such a request to the configuration device 650 or the diabetes management device 104. In various implementations, the computer software entity 536 may be updated automatically when the diabetes management device 104 and the configuration device 650 are connected. The connection may be wired or wireless.

To update the computer software entity 536, the configuration device 650 may replace one or more portions of the computer software entity 536 or replace the computer software entity 536 with another computer software entity. The configuration device 650 updates the computer software entity 536 with data downloaded from a data distribution server 654.

Before updating the computer software entity 536, the configuration device 650 may obtain the device/user certificate from the diabetes management device 104. The configuration device 650 may verify that the diabetes management device 104 is registered and authorized to be updated. In various implementations, the authentication/verification may be performed via communication between the configuration device 650 and an authentication server 658. The authentication server 658 may be different than the data distribution server 654.

The device/user certificate may include an expiration. If the device/user certificate has previously expired, the configuration device 650 may not allow the computer software entity 536 to be updated. The configuration device 650 may also receive a first certificate revocation list (CRL) from the authentication server 658. A CRL may also be referred to as a revocation list.

The first CRL may include a list of non-expired device/user certificates that are ineligible to receive data via the data distribution server 654. The first CRL may also include expired device/user certificates that are ineligible to receive data via the data distribution server 654. If the device/user certificate of the diabetes management device 104 is on the first CRL (e.g., the same as one of the device/user certificates in the first CRL), the configuration device 650 may not allow the computer software entity 536 to be updated. If the device/user certificate is not on the first CRL, the configuration device 650 may update the diabetes management device 104 based on data from the data distribution server 654.

The configuration device 650 may also perform one or more actions when the device/user certificate of the diabetes management device 104 is on the first CRL. For example only, the configuration device 650 may attempt to obtain a new (non-expired) device/user certificate for the diabetes management device 104, display an indication that the diabetes management device 104 is not eligible for updating (e.g., via a display of the configuration device 650 and/or a display of the diabetes management device 104), and/or perform one or more other suitable actions.

Data for updating authorized and registered handheld medical devices including the diabetes management device 104 may be stored in a database 672. The database 672 can be accessed by the data distribution server 654. Device specific data for each authorized and registered handheld medical device may also be stored in the database 672. For example only, each time the diabetes management device 104 is updated, data for the diabetes management device 104 stored in the database 672 is updated such that the database 672 includes data indicative of the last known characteristics of each handheld medical device.

The configuration device 650 may selectively obtain software data from the data distribution server 654 for the diabetes management device 104. The software data from the data distribution server 654 indicates a current computer software entity that the database 672 has record of as being installed and executed by the diabetes management device 104. The configuration device 650 may also obtain the software certificate from the diabetes management device 104. The configuration device 650 may compare the version data obtained from the data distribution server 654 with the version data indicated within the software certificate obtained from the diabetes management device 104. The configuration device 650 may notify the data distribution server 654 if the two differ. If the version data is different, the configuration device 650 may perform one or more protective actions. Example protective actions are discussed further below.

The configuration device 650 may also obtain a second CRL from the data distribution server 654. The second CRL may include a list of computer software entities that are not to be executed by any of a group of handheld medical devices including the diabetes management device 104. The configuration device 650 may determine whether the software certificate for the computer software entity 536 is in the second CRL.

If the software certificate for the computer software entity 536 is in the second CRL, the configuration device 650 may perform one or more protective actions. For example only, the configuration device 650 may prevent the processor module 504 from executing the computer software entity 536 in the future. The configuration device 650 may prevent the processor module 504 from executing the computer software entity 536, for example, by changing the state of a flag or other indicator that the processor module 504 checks before executing any portion of the computer software entity 536. For another example only, the configuration device 650 may display a predetermined message on the display of the diabetes management device 104 and/or the configuration device 650. For yet another example only, the configuration device 650 may prompt a user to input an acknowledgement. For another example only, the configuration device 650 may update the computer software entity 536 based on another computer software entity associated with a software certificate that is not in the second CRL.

The configuration device 650 may receive data indicating possible upgrades that are available for the diabetes management device 104. The configuration device 650 may display the possible upgrades for selection by a user. The configuration device 650 may display the possible upgrades via the display of the diabetes management device 104 and/or the display of the computer 106.

A user may select one or more of the possible updates. The configuration device 650 may update data stored in the datastore 532 of the diabetes management device 104 based on the selected possible updates. For example only, the configuration device 650 may update the computer software entity 536 based on a selected computer software entity. The configuration device 650 may also perform an authentication to verify that the user is eligible to update the diabetes management device 104. The configuration device 650 may refrain from updating the diabetes management device 104 if the user is not eligible to update the diabetes management device 104. After an update, the processor module 504 executes the selected computer software entity to control the functionality of the diabetes management device 104. The configuration device 650 may update the device data 540, the cryptography data 544, and/or other suitable data to reflect the update.

After updating the diabetes management device 104, the configuration device 650 requests the data distribution server 654 update the data stored in the database 672 for the diabetes management device 104 to reflect the update to the diabetes management device 104. In this manner, the data stored in the database 672 for the diabetes management device 104 reflects the present state of the computer software entity 536 installed on the diabetes management device 104 for execution by the diabetes management device 104.

Figure 7:
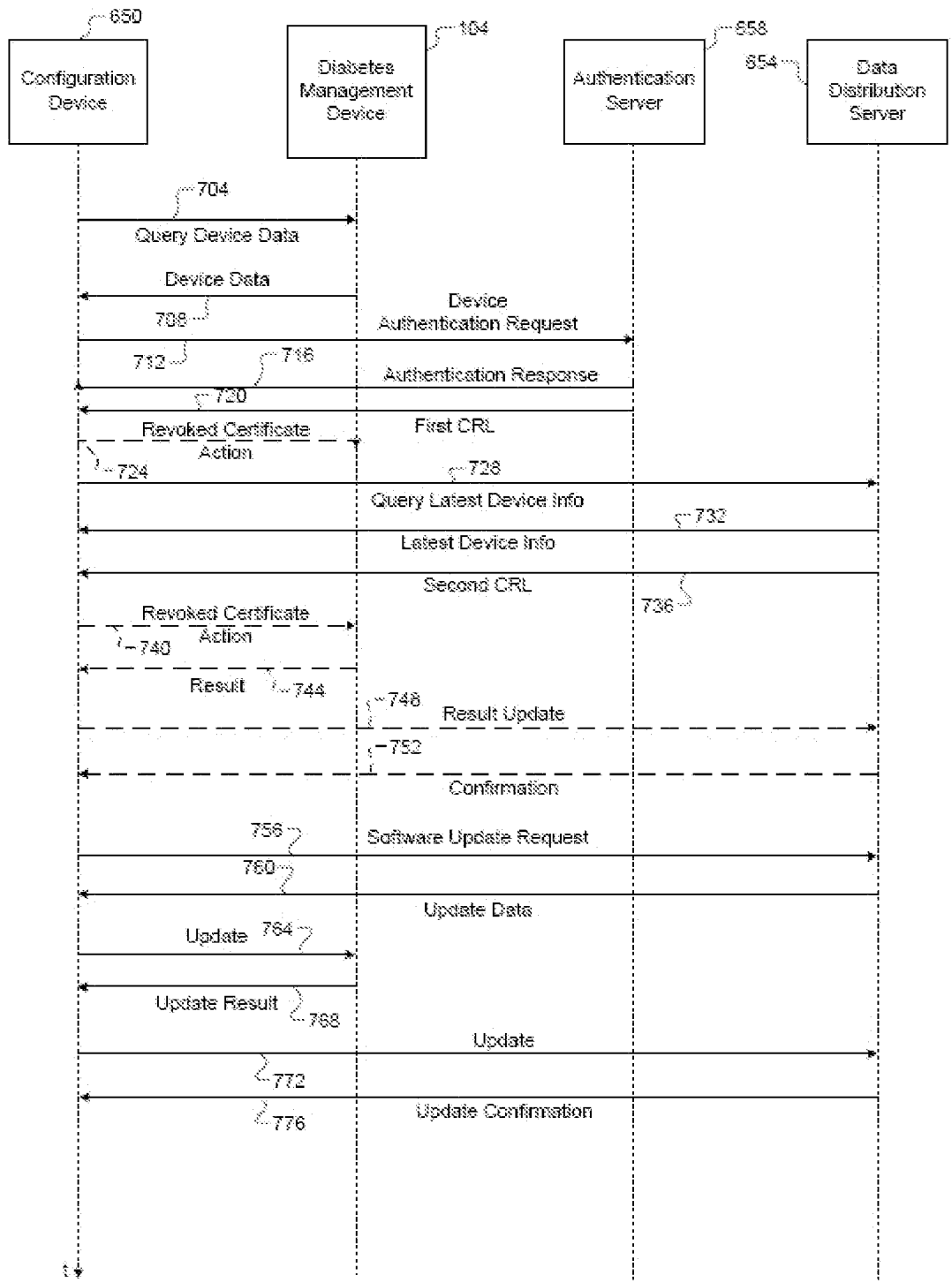
FIG. 7 includes an example illustration of a method of controlling distribution of data to a handheld medical device.

Referring now to FIG. 7, an example method of regulating distribution of data to handheld medical devices is presented. The configuration device 650 may query 704 the diabetes management device 104 for device data stored in the data store 532 of the diabetes management device 104. For example only, the configuration device 650 may query the diabetes management device 104 for the device/user certificate and the software certificate of the diabetes management device 104. The configuration device 650 may generate the query 704 in response to an update request (not shown), automatically at a time when the diabetes management device 104 is connected to the configuration device 650, or at another suitable time. The diabetes management device 104 transmits device data 708 to the configuration device 650 in response to the query 704.

The configuration device 650 may transmit an authentication request 712 to the authentication server 658. The configuration device 650 may transmit the authentication request 712, for example, in conjunction with authenticating the device/user certificate and verifying that the diabetes management device 104 is eligible to receive updates from the data distribution server 654. The configuration device 650 may transmit the authentication request 712 or another authentication request, for example, in conjunction with authenticating a user of the configuration device 650 and verifying that the user is eligible to update the diabetes management device 104 and/or the type of data that is to be updated. The authentication server 658 may transmit an authentication response 716 based on a result of the authentication and verification. In various implementations, the authentication server 658 may transmit the necessary data to the configuration device 650 for the configuration device 650 to perform the authentication and verification, or the necessary data may be previously stored in memory of the configuration device 650. The authentication response 716 may indicate whether the authentication and verification passed or failed.

The authentication server 658 may also transmit the first CRL 720 to the configuration device 650 in response to the authentication request 712. The configuration device 650 compares the device/user certificate with the first CRL 720. If the device/user certificate is in the first CRL 720, the configuration device 650 may take one or more revoked certificate actions 724.

If the device/user certificate is not on the first CRL 720, the configuration device 650 may transmit a latest info query 728 to the data distribution server 654. The latest info query 728 may request the latest data that is stored in the database 672 for the diabetes management device 104. More specifically, the latest info query 728 may request the latest information that is stored in the database 672 regarding a computer software entity stored in the datastore 532 of the diabetes management device 104.

The data distribution server 654 retrieves latest device info 732 in response to the request and transmits the latest device info 732 to the configuration device 650. The data distribution server 654 also transmits the second CRL 736 to the configuration device 650. The configuration device 650 may transmit a notification (not shown) to the data distribution server 654 if the computer software entity 536 stored in the datastore 532 is different than the computer software entity indicated via the last device info 732.

The configuration device 650 compares the software certificate stored in the datastore 532 of the diabetes management device 104 with the second CRL 736. If the software certificate is in the second CRL 736, the configuration device 650 may take one or more protective actions 740, such as updating the computer software entity 536 based on another computer software entity. Once completed, the diabetes management device 104 may transmit a result 744 of the one or more protective actions 740 to the configuration device 650. The configuration device 650 may transmit a result update 748 to the data distribution server 654. The result update 748 may indicate the result 744 of the one or more protective actions 740. The data distribution server 654 may update the data stored in the database 672 for the diabetes management device 104 based on the result. The data distribution server 654 may transmit a confirmation 752 to the configuration device 650 when the data stored in the database 672 has been updated.

If the software certificate is not in the second CRL 736, the configuration device 650 may selectively transmit a software update request 756 to the data distribution server 654. The software update request 756 may indicate data (e.g., a computer software entity or update) to be stored to the datastore 532 of the diabetes management device 104. The data distribution server 654 may retrieve the indicated data from the database 672 in response to the request. The data distribution server 654 may transmit the retrieved data 760 for updating the diabetes management device 104 to the configuration device 650.

The configuration device 650 may update 764 the diabetes management device 104 based on the data 760. More specifically, the configuration device 650 may load the data 760 into the datastore 532 of the diabetes management device 104. The processor module 504 can then execute the data 760 to control the operation of the diabetes management device 104.

Once completed, the diabetes management device 104 may transmit a result 768 of the updating to the configuration device 650. The result 768 may indicate, for example, whether the updating was successful. The configuration device 650 may transmit a result update 772 to the data distribution server 654. The result update 748 may indicate the result 768 of the updating. The data distribution server 654 may update the data stored in the database 672 for the diabetes management device 104 based on the result update 748. The data distribution server 654 may transmit a confirmation 776 to the configuration device 650 when the data stored in the database 672 has been updated.

A method of protecting a handheld medical device from executing a computer software entity installed in memory of the handheld medical device for execution by the handheld medical device, comprises: receiving a revocation list from a remote data server at a configuration device, the revocation list including N cryptographic certificates associated with N computer software entities, respectively, that are not to be executed by any of a group of medical devices including a handheld medical device, wherein N is an integer greater than or equal to zero; receiving data from the handheld medical device at the configuration device, the data including a cryptographic certificate that is associated with a given computer software entity that is presently installed in memory of the handheld medical device for execution by the handheld medical device; comparing the cryptographic certificate with the revocation list; and selectively executing a protective function by the configuration device when the cryptographic certificate is the same as one of the N cryptographic certificates of the revocation list.

In other features, the protective function includes disabling the given computer software entity from execution by the handheld medical device.

In still other features, the handheld medical device includes a handheld blood glucose management device.

In further features, the protective function includes displaying a predetermined message on a display of the handheld medical device.

In still further features, the protective function further includes prompting a user to input an acknowledgement.

In other features, the protective function includes uploading a second computer software entity to the memory of the handheld medical device for execution by the handheld medical device, and the second computer software entity is different than the given computer software entity.

In still other features, the method further comprises: receiving device data at the configuration device, the device data including an identifier of the handheld medical device; and selecting the second computer software entity from a plurality of computer software entities based on the identifier.

In further features, the method further comprises verifying that the second computer software entity is not the same as one of the N cryptographic certificates of the revocation list.

A method of regulating updatability of data stored in memory of a handheld medical device, comprises: receiving a revocation list from a first remote data server at a configuration device, the revocation list including N cryptographic certificates associated with N handheld medical devices, respectively, that are to be denied access to data accessible via a second remote data server, wherein N is an integer greater than or equal to zero; receiving data from a handheld medical device at the configuration device, the data including a cryptographic certificate that is associated with the handheld medical device; comparing the cryptographic certificate with the revocation list; and selectively updating the handheld medical device with data from the second remote data server after a determination that the cryptographic certificate is not the same as any of the N cryptographic certificates of the revocation list.

In other features, the first and second remote data servers are different.

In still other features, the method further comprises, after the determination that the cryptographic certificate is not the same as any of the N cryptographic certificates of the revocation list: receiving a second revocation list from the second remote data server at a configuration device, the second revocation list including M cryptographic certificates associated with M computer software entities, respectively, that are not to be executed by any of a group of medical devices including the handheld medical device, wherein M is an integer greater than or equal to zero, and wherein the data further includes a second cryptographic certificate that is associated with a given computer software entity that is presently installed in memory of the handheld medical device for execution by the handheld medical device; and comparing the second cryptographic certificate with the second revocation list.

In further features, the method further comprises selectively performing a protective function by the configuration device in response to a determination that the second cryptographic certificate is the same as one of the M cryptographic certificates in the second revocation list.

In still further features, the protective function includes disabling the given computer software entity from execution by the handheld medical device.

In other features, the protective function includes displaying a predetermined message on a display of the handheld medical device.

In still other features, the protective function further includes prompting a user to input an acknowledgement.

In further features, the protective function includes uploading a second computer software entity to the memory of the handheld medical device for execution by the handheld medical device, and the second computer software entity is different than the given computer software entity.

In still further features, the method further comprises selecting the second computer software entity from a plurality of computer software entities based on the handheld medical device.

In other features, the method further comprises verifying that the second computer software entity is not the same as any of the M cryptographic certificates of the second revocation list.

In still other features, the method further comprises avoiding updating the handheld medical device after a determination that the cryptographic certificate is the same as one of the N cryptographic certificates of the revocation list.

In further features, the handheld medical device includes a handheld blood glucose management device.

The broad teachings of the disclosure can be implemented in a variety of forms. Therefore, while this disclosure includes particular examples, the true scope of the disclosure should not be so limited since other modifications will become apparent to the skilled practitioner upon a study of the drawings, the specification, and the following claims.

What is claimed is:

1. A method of protecting a handheld medical device from executing a computer software entity installed in memory of the handheld medical device for execution by the handheld medical device, comprising:

receiving a revocation list from a remote data server at a configuration device, the revocation list including N cryptographic certificates associated with N computer software entities, respectively, that are not to be executed by any of a group of medical devices including a handheld medical device, wherein N is an integer greater than or equal to zero;

receiving data from the handheld medical device at the configuration device, the data including a cryptographic certificate that is associated with a given computer software entity that is presently installed in a memory of the handheld medical device for execution by the handheld medical device;

comparing the cryptographic certificate with the revocation list; and executing a protective function by the configuration device when the cryptographic certificate is the same as one of the N cryptographic certificates of the revocation list.

2. The method of claim 1 wherein the protective function includes disabling the given computer software entity from execution by the handheld medical device.

3. The method of claim 1 wherein the handheld medical device includes a handheld blood glucose management device.

4. The method of claim 1 wherein the protective function includes displaying a predetermined message on a display of the handheld medical device.

5. The method of claim 4 wherein the protective function further includes prompting a user to input an acknowledgement.

6. The method of claim 1 wherein the protective function includes uploading a second computer software entity to the memory of the handheld medical device for execution by the handheld medical device, and wherein the second computer software entity is different than the given computer software entity.

7. The method of claim 6 further comprising:

receiving device data at the configuration device, the device data including an identifier of the handheld medical device; and selecting the second computer software entity from a plurality of computer software entities based on the identifier.

8. The method of claim 7 further comprising verifying that the second computer software entity is not the same as one of the N cryptographic certificates of the revocation list.

9. A method of regulating updatability of data stored in memory of a handheld medical device, comprising:

receiving a revocation list from a first remote data server at a configuration device, the revocation list including N cryptographic certificates associated with N handheld medical devices, respectively, that are to be denied access to data accessible via a second remote data server, wherein N is an integer greater than or equal to zero;

receiving data from a handheld medical device at the configuration device, the data including a cryptographic certificate that is associated with the handheld medical device;

comparing the cryptographic certificate with the revocation list; and updating the handheld medical device with data from the second remote data server after a determination that the cryptographic certificate is not the same as any of the N cryptographic certificates of the revocation list.

10. The method of claim 9 wherein the first and second remote data servers are different.

11. The method of claim 9 further comprising, after the determination that the cryptographic certificate is not the same as any of the N cryptographic certificates of the revocation list:

receiving a second revocation list from the second remote data server at a configuration device, the second revocation list including M cryptographic certificates associated with M computer software entities, respectively, that are not to be executed by any of a group of medical devices including the handheld medical device, wherein M is an integer greater than or equal to zero, and wherein the data further includes a second cryptographic certificate that is associated with a given computer software entity that is presently installed in memory of the handheld medical device for execution by the handheld medical device; and comparing the second cryptographic certificate with the second revocation list.

12. The method of claim 11 further comprising selectively performing a protective function by the configuration device in response to a determination that the second cryptographic certificate is the same as one of the M cryptographic certificates in the second revocation list.

13. The method of claim 12 wherein the protective function includes disabling the given computer software entity from execution by the handheld medical device.

14. The method of claim 12 wherein the protective function includes displaying a predetermined message on a display of the handheld medical device.

15. The method of claim 14 wherein the protective function further includes prompting a user to input an acknowledgement.

16. The method of claim 12 wherein the protective function includes uploading a second computer software entity to the memory of the handheld medical device for execution by the handheld medical device, and wherein the second computer software entity is different than the given computer software entity.

17. The method of claim 16 further comprising selecting the second computer software entity from a plurality of computer software entities based on the handheld medical device.

18. The method of claim 16 further comprising verifying that the second computer software entity is not the same as any of the M cryptographic certificates of the second revocation list.

19. The method of claim 9 further comprising avoiding updating the handheld medical device after a determination that the cryptographic certificate is the same as one of the N cryptographic certificates of the revocation list.

20. The method of claim 9 wherein the handheld medical device includes a handheld blood glucose management device.

* * * * *